(12) United States Patent
David

(10) Patent No.: US 7,491,221 B2
(45) Date of Patent: Feb. 17, 2009

(54) MODULAR POLYAXIAL BONE SCREW AND PLATE

(75) Inventor: Jérôme David, Bordeaux (FR)

(73) Assignee: Stryker Spine (FR)

( * ) Notice: Subject to any disclaimer, the term of this patent is extended or adjusted under 35 U.S.C. 154(b) by 35 days.

(21) Appl. No.: 10/806,736

(22) Filed: Mar. 23, 2004

(65) Prior Publication Data
US 2005/0216001 A1 Sep. 29, 2005

(51) Int. Cl.
*A61B 17/80* (2006.01)
*A61B 17/70* (2006.01)
*A61B 17/86* (2006.01)

(52) U.S. Cl. .................. 606/288; 606/266; 606/307; 606/316

(58) Field of Classification Search .............. 606/61, 606/69–71, 73, 246–299, 301–324, 300
See application file for complete search history.

(56) References Cited

U.S. PATENT DOCUMENTS

| | | | |
|---|---|---|---|
| 4,836,196 A * | 6/1989 | Park et al. ............... | 606/61 |
| 5,129,899 A | 7/1992 | Small et al. | |
| 5,234,431 A | 8/1993 | Keller et al. | |
| 5,261,910 A | 11/1993 | Warden et al. | |
| 5,395,372 A | 3/1995 | Holt et al. | |
| 5,486,176 A | 1/1996 | Hildebrand et al. | |
| 5,501,684 A | 3/1996 | Schlapfer et al. | |
| 5,531,745 A | 7/1996 | Ray | |
| 5,575,791 A | 11/1996 | Lin | |
| 5,582,612 A | 12/1996 | Lin | |
| 5,591,166 A | 1/1997 | Bernhardt et al. | |
| 5,607,428 A | 3/1997 | Lin | |
| 5,613,967 A | 3/1997 | Engelhardt et al. | |
| 5,613,968 A * | 3/1997 | Lin ........................ | 606/61 |
| 5,672,176 A | 9/1997 | Biedermann et al. | |
| 5,728,127 A | 3/1998 | Asher et al. | |
| 5,800,435 A * | 9/1998 | Errico et al. ............ | 606/61 |
| 5,814,046 A * | 9/1998 | Hopf ...................... | 606/61 |

(Continued)

FOREIGN PATENT DOCUMENTS

DE 20202049 U1 * 6/2002

*Primary Examiner*—Eduardo C Robert
*Assistant Examiner*—Richard Shaffer
(74) *Attorney, Agent, or Firm*—Lerner, David, Littenberg, Krumholz & Mentlik, LLP

(57) ABSTRACT

An orthopedic bone plate system having a bone plate for placement adjacent one or more vertebral bodies. The bone plate has a first aperture extending along a longitudinal axis and an upper and lower surface. The bone plate system further includes a sliding element having a top portion and a base portion and an aperture extending along a central axis. The sliding element is adapted for being placed adjacent to the bone plate aperture. The system preferably includes a bone fastener having a longitudinal axis which is adapted for connecting the bone plate to a vertebral body. The bone fastener includes a stem and a bone engaging portion. The diameter of the stem may be less than a cross section of the sliding element aperture so that the stem may be oriented within the sliding element aperture at a plurality of angles. The system may further include a stopping element engageable with the sliding element base portion. The stopping element includes a bore adapted for receiving the stem portion of the bone fastener. The orthopedic bone plate system may also include a locking element engageable with the top portion of the sliding element and having a bore adapted for receiving the stem portion of the bone fastener.

31 Claims, 9 Drawing Sheets

U.S. PATENT DOCUMENTS

| | | | |
|---|---|---|---|
| 5,891,145 A | 4/1999 | Morrison et al. | |
| 5,902,303 A | 5/1999 | Eckhof et al. | |
| 5,964,761 A | 10/1999 | Kambin | |
| 6,022,350 A | 2/2000 | Ganem et al. | |
| 6,066,140 A | 5/2000 | Gertzbein et al. | |
| 6,080,156 A | 6/2000 | Asher et al. | |
| 6,206,882 B1 | 3/2001 | Cohen | |
| 6,235,033 B1 | 5/2001 | Brace et al. | |
| 6,280,443 B1 | 8/2001 | Gu et al. | |
| 6,280,445 B1 | 8/2001 | Morrison et al. | |
| 6,287,309 B1* | 9/2001 | Baccelli et al. | 606/61 |
| 6,290,703 B1 | 9/2001 | Ganem et al. | |
| 6,302,883 B1 | 10/2001 | Bono | |
| 6,315,779 B1* | 11/2001 | Morrison et al. | 606/69 |
| 6,379,354 B1 | 4/2002 | Rogozinski | |
| 6,379,357 B1 | 4/2002 | Bernstein et al. | |
| 6,432,108 B1 | 8/2002 | Burgess et al. | |
| 6,520,990 B1 | 2/2003 | Ray | |
| 6,575,975 B2 | 6/2003 | Brace et al. | |
| 6,585,738 B1 | 7/2003 | Mangione et al. | |
| 6,613,053 B1 | 9/2003 | Collins et al. | |
| 6,641,583 B2 | 11/2003 | Shluzas et al. | |
| 6,689,133 B2 | 2/2004 | Morrison | |
| 2002/0026194 A1 | 2/2002 | Morrison et al. | |
| 2002/0049446 A1 | 4/2002 | Harkey et al. | |
| 2002/0143328 A1 | 10/2002 | Shluzas et al. | |
| 2002/0193795 A1 | 12/2002 | Gertzbein et al. | |
| 2003/0045875 A1 | 3/2003 | Bertranou et al. | |
| 2003/0045878 A1* | 3/2003 | Petit et al. | 606/61 |
| 2003/0073998 A1* | 4/2003 | Pagliuca et al. | 606/61 |
| 2003/0105462 A1 | 6/2003 | Haider | |
| 2003/0153919 A1 | 8/2003 | Harris | |

* cited by examiner

FIG. 5A
FIG. 5B
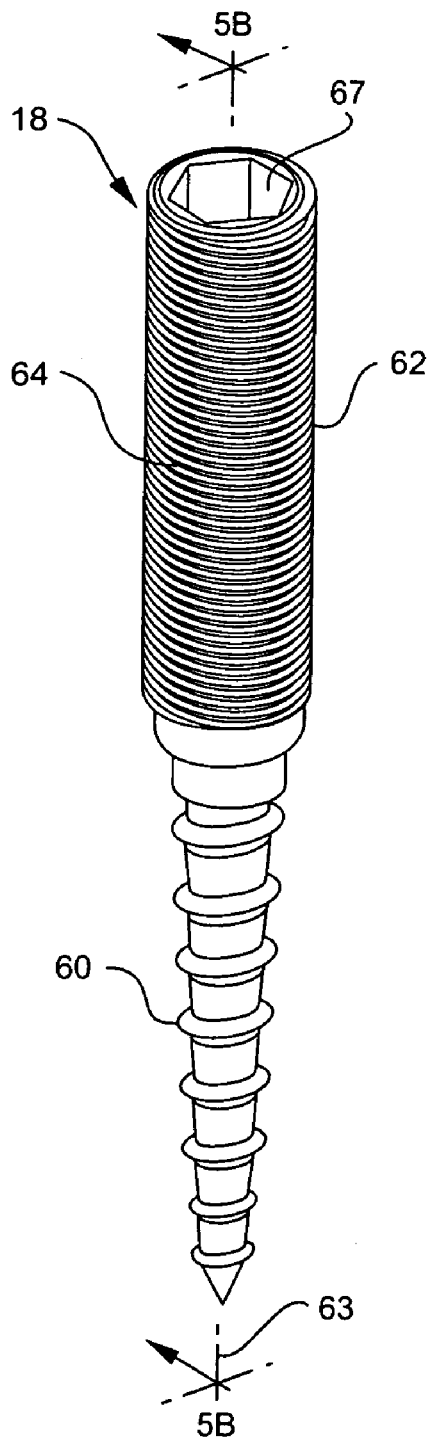
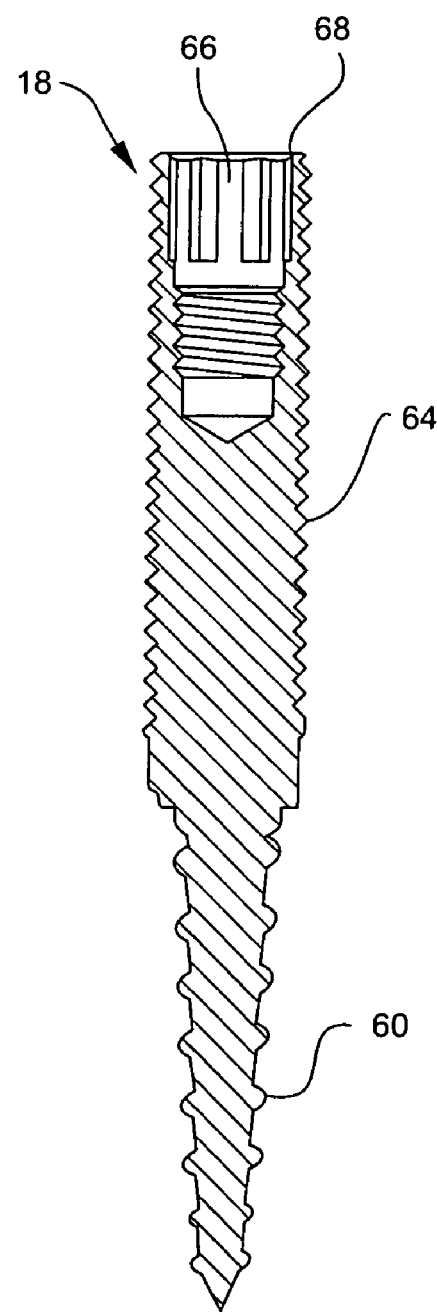

140
MODULAR POLYAXIAL BONE SCREW AND PLATE

BACKGROUND OF THE INVENTION

The present invention relates generally to an orthopedic implant assembly system and in particular to a multi-axial bone plate system.

Orthopedic implant assembly systems having a multi-axial bone plate are known in the art and include at least two pedicular screws anchored in adjacent vertebrae to be treated and a connecting plate designed to connect the screw heads together in a rigid manner. Previous references, such as U.S. Pat. Nos. 6,287,309 and 5,486,176 disclose a system of this kind in which each pedicular screw has a hexagonal section part for inserting the screw into the bone and on top of which is a threaded shank. The plate has a plurality of oblong openings through which the various threaded shanks can be inserted and an open groove on its bottom face to prevent rotation of the hexagonal part of each pedicular screw.

Each pedicular screw is associated with a stirrup through which the threaded shank of the screw also passes and which straddles the top of the plate. Finally, a nut is screwed onto the threaded shank to trap and immobilize the plate with the stirrup on top of it, between it and the hexagonal portion of the screw.

Further, known systems include at least two pedicular screws and a connecting plate for linking screws together in essentially a rigid manner. Each screw has a bone anchor threaded part, a non-circular section head, and a threaded end shank adapted to cooperate with a nut. The plate has at least one opening adapted to have the threaded end shank of the screw pass through it and be trapped between the screw head and the nut. Raised patterns are provided on the top face of the plate and on the bottom face of the stirrup to prevent longitudinal sliding of the plate relative to the screw. A locking member is also provided for preventing relative angular movement between the heads of the screws and the connecting plate. The locking member is adapted to be inserted between the plate and the screw head and includes a bar through which the threaded end shank of the screw passes. The locking member further includes a first locking cooperation of shapes with the screw head and a second cooperation of shapes with the plate.

Although these systems are generally satisfactory, they nevertheless have certain drawbacks. Specifically, in certain systems, raised patterns have to be provided to prevent sliding because the plate and the stirrup cooperate via two plane faces in compression. Absence of the raised patterns would lead to the risk of entirely unacceptable relative movement of the vertebrae. The machining required to create these raised patterns significantly increases the mean cost of the plates and the stirrups.

Additionally, the raised patterns can impede fine adjustment of the system. For example, there are only a particular number of discrete mutually engageable positions of the plate and the stirrup, i.e., a particular number of discrete distances between the screws. Moreover, if the nut is over-tightened before the final tightening, lateral sliding of the plate and the stirrup during adjustment may be impeded.

Some of the drawbacks associated with other designs include that the first locking cooperation and second cooperation of shapes with the plate forbid and restrict plate movement in an anterior and posterior direction once the pedicle screw has been rested against the plate member.

Additionally, most plate systems include a bone fastener with a threaded end extended from the vertebral body. In order to lock the screw relative to the plate, a nut must be used in combination with the screw. The problem associated with this design is that if the screw is not placed at the correct depth within the vertebral body, the assembly must be disassembled in order to either increase or decrease the depth of the screw in the vertebrae. An additional problem results from this action due to the fact that once the screw has been placed too deep within the vertebral body, the screw might be less securely locked within the vertebral body when the screw is backed out and placed in its correct position.

Other shortcomings of known systems include angled orientations in the sagittal direction are not permitted due to the shape of the locking cooperation members.

SUMMARY OF THE INVENTION

An orthopedic bone plate system having a bone plate for placement adjacent one or more vertebral bodies. The bone plate has a first aperture extending along a longitudinal axis and an upper and lower surface. The bone plate system further includes a sliding element having a top portion and a base portion and an aperture extending along a central axis. The sliding element is adapted for being placed adjacent to the bone plate aperture.

The system preferably includes a bone fastener having a longitudinal axis which is adapted for connecting the bone plate to a vertebral body. The bone fastener includes a stem and a bone engaging portion. The diameter of the stem may be less than a cross section of the sliding element aperture so that the stem may be oriented within the sliding element aperture at a plurality of angles.

The system may further include a stopping element engageable with the sliding element base portion. The stopping element includes a bore adapted for receiving the stem portion of the bone fastener. The orthopedic bone plate system may also include a locking element engageable with the top portion of the sliding element and having a bore adapted for receiving the stem portion of the bone fastener.

The sliding element may also include a compression member and a locking member. The compression member having a top portion while the locking member includes a base portion. The compression member may be adapted to engage the locking member. A plurality of fingers may extend in a direction parallel to the central axis of the compression member from the top portion toward the base portion. The fingers may be tapered inwardly toward the central axis. The top and base portions may include an inwardly tapered wall. Further, the top portion may also include a radially outwardly extending curve wall while the base portion may also include a radially outwardly extending curve wall.

In one embodiment, the fingers have a ridge extending at least partially around an outer circumference thereof. The ridge is adapted to engage a lip extending at least partially around an inner circumference of the base portion.

The sliding element aperture may have a minimum diameter greater than the maximum diameter of the stem of the bone fastener. A locking element may include a base and a cap. The locking element may also have a concave wall at least partly surrounding the locking element bar. Further, the locking element may include threads mateable to threads disposed on the stem of the bone fastener. The locking element may threadably engage the stem of the bone fastener wherein the concave surface of the locking element is adapted for cooperating with the sliding elements spherical top portion at a plurality of different angles.

In additional embodiments, the stopping element may have an inner spherical wall at least partially surrounding the stopping element bore wherein the stopping element inner spherical wall is adapted for cooperating with a spherical surface of the sliding element base portion at a plurality of different angles. The stopping element may further include threads mateable to threads on the stem of the bone fastener. In a preferred embodiment of the present invention, the stopping element, locking nut and bone fastener are adapted for being locked on the sliding element relative to one another wherein the stopping element, locking element and the bone fastener may be positioned about the sliding element aperture at a plurality of different angles.

The bone plate may further include an interior wall adapted for cooperating with the top and base portion of the sliding element. The top portion and base portion may also include a radially extending shoulder adapted for cooperating with the upper and lower surface of the bone plate. The sliding element may be adapted for sliding along the bone plate aperture along the longitudinal axis.

The orthopedic bone plate system may further include a first set of threads disposed on the stem portion and a second and third set of threads disposed on the stopping element bore and the locking element bore respectively. The first set of threads engage the second and third set of threads when the stem portion is placed within the locking element bore and the stopping element bore.

The bone fastener may further include a top surface having a recess adapted for engaging an instrument or tool. Preferably, the recess is capable of being accessed after the bone plate assembly is assembled.

The bone plate may have at least two apertures separated by a bridge extending transverse to the longitudinal axis. Further, the bone plate may be curved in an anterior and posterior direction.

The present invention also includes a system for coupling a bone fastener to a bone plate having a bone plate with a bone facing surface and an elongated opening therethrough extending along a longitudinal access generally parallel to the bone facing surface. An insert slidable in the elongated opening may also be included. The insert including a first part with a part spherical outer surface and an internal bore extending along an axis transverse to the elongated opening in the bone plate. Further, the system may include a bone fastener having a first bone engaging portion and a second portion for extending through the bore and the insert and a locking element mounted on the second portion of the fastener. The locking element having a parts spherical surface for engaging the spherical outer surface of the insert. The locking element moves toward the bone plate along the second portion of the fastener for engaging and moving the insert first part into engagement with the bone plate.

The insert may further include a second part mounted on the fastener and engageable with the bone facing plate surface. The first and second insert parts move towards one another for clamping the bone plate therebetween.

The system may further include a stopping element mounted on the fastener of the second portion and engageable with a bone facing surface of the insert second part. The second portion of the bone fastener may be threaded and the stop element and the locking element may include threaded bores for threadably engaging the threads of the fastener of the second portion. The first and second insert parts may each have outer tapered surfaces for engaging tapered surface in the aperture.

The present invention also includes a method for implanting an orthopedic implant system in a bone preferably including the steps of engaging a bone engaging portion of a bone fastener having a first bone engaging portion and second portion extending from the bone engaging portion along a longitudinal axis to a bone. A bone plate may be provided having a bone facing surface and an elongated opening therethrough extending along a longitudinal axis generally parallel to the bone facing surface. The present method of operation may further include placing an insert slidable in the elongated opening on the bone fastener. The insert having a first part with a spherical outer surface and an internal bore extending along an axis transverse to the elongated opening in the plate. The insert may be positioned down the bone fastener second portion wherein the insert bore is adapted for receiving the second portion. Further, the bone plate and the insert may be oriented into a desired position with respect to the bone fastener. Further, a locking element may be mounted on a second portion of the fastener. The locking element having a spherical surface for engaging the spherical outer surface of the insert. The locking element moves toward the bone plate along the second portion of the fastener for engaging and moving the insert first part into engagement with the bone plate.

The method may further include the step of adjusting the bone fastener relative to the bone after the insert receive the second portion. The insert may also include a second part having a bore for receiving the bone fastener second portion. The second part being engageable with the bone facing plate surface wherein said first and second insert parts are moveable towards one another for clamping the bone plate therebetween.

A method may further include the step of mounting a stop element on the fastener second portion and engageable with a bone facing surface of the insert second part

BRIEF DESCRIPTION OF THE DRAWINGS

The present invention will be better understood on reading the following detailed description of non-limiting embodiments thereof, and on examining the accompanying drawings, in which:

FIG. 5a is a perspective view of a bone fastener.

FIG. 5b is a cross-sectional view of the bone fastener illustrated in FIG. 5a along lines 5b-5b;

FIG. 7b is a cross-sectional view of the sliding element illustrated in FIG. 7a;

FIG. 8b is a cross-sectional view of the stopping element in FIG. 8a;

FIG. 9b is a cross-sectional view of the locking element illustrated in FIG. 9a.

DETAILED DESCRIPTION

Figure 1:
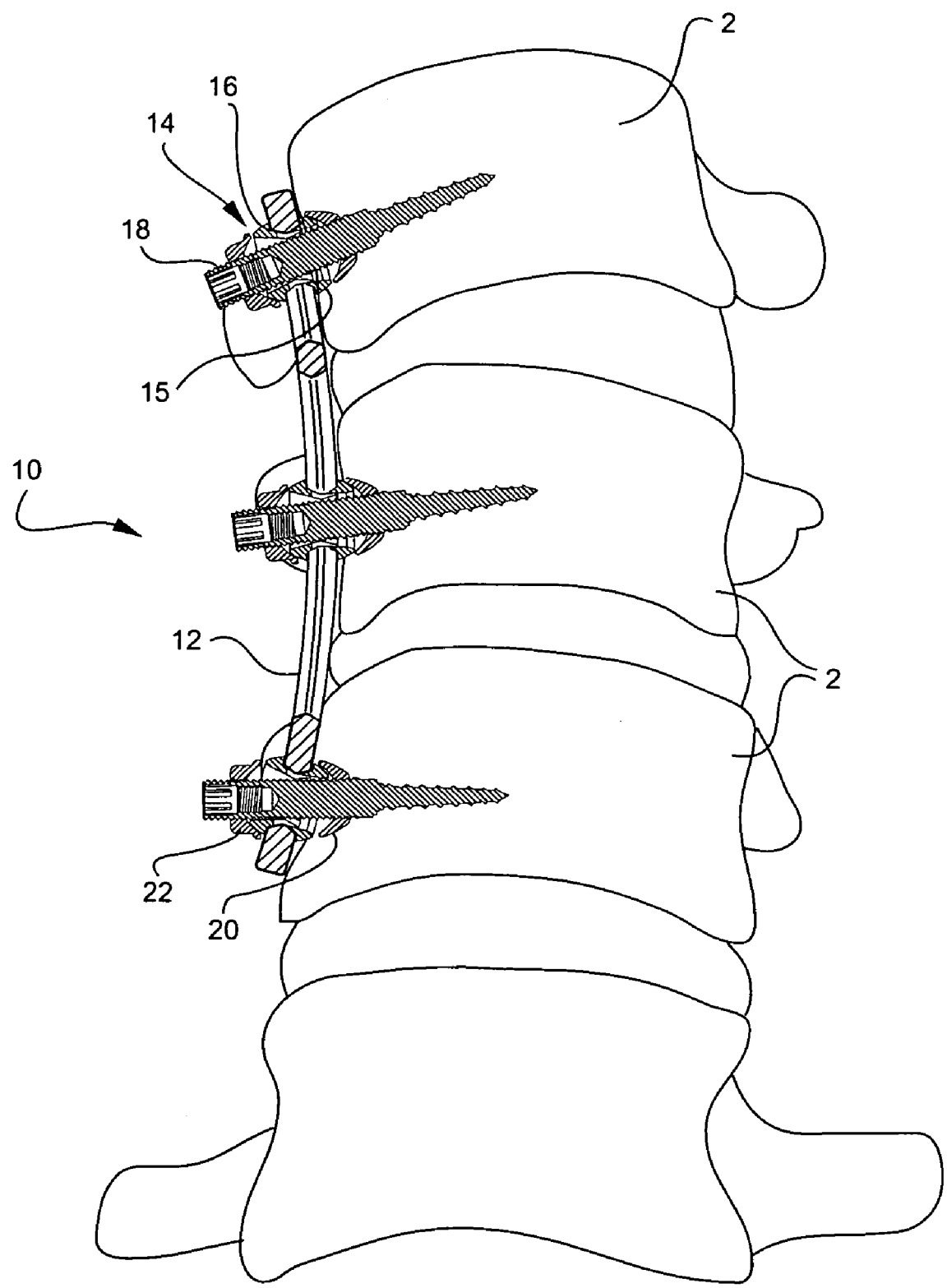
FIG. 1 is a schematic drawing in cross-section illustrating an embodiment of the orthopedic implant of the present invention implanted into a vertebrae.

For the purposes of promoting and understanding the principles of the present invention, reference will now be made to the embodiment illustrated in the drawings and specification language will be used to describe the same. Nevertheless, by those skilled in the art, it will be understood that no limitation of the scope of the present invention is thereby intended, and further changes in the illustrated device may be made without deviating from the scope of the present invention.

As shown in FIG. 1, the spinal implant system 10 of the present invention includes a plate 12, a sliding element 14 having a top portion 16 and a bottom portion 15, a bone fastener 18, a stopping element 20, and a locking element 22. As shown in the figures, bone fasteners 18 function to anchor plate 12 to vertebral bodies 2 and may be oriented at an angle with regard to the vertebral body.

Figure 2:
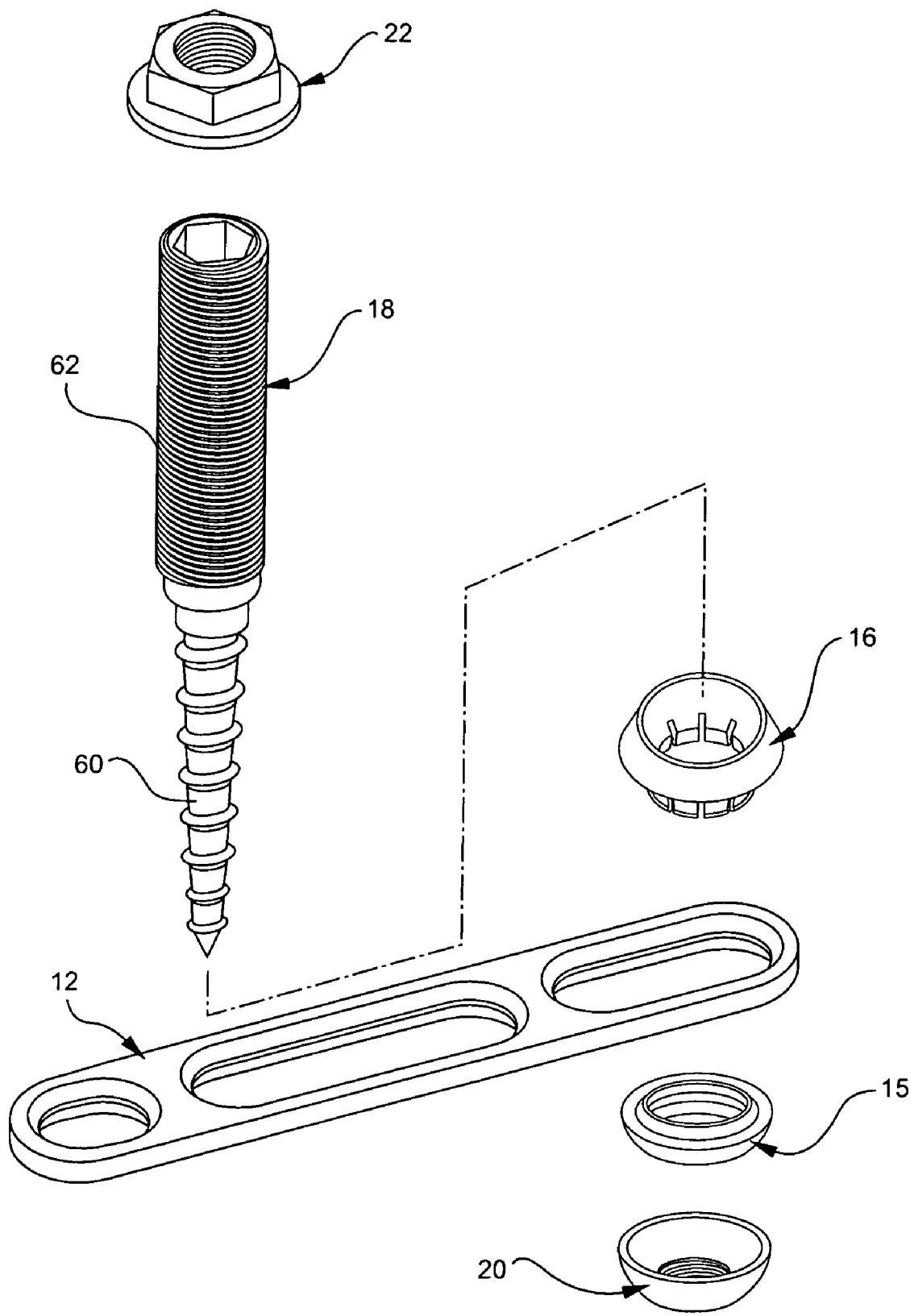
FIG. 2 is an exploded perspective view of one embodiment of the orthopedic system of the present invention.

FIG. 2 details the assembly of the parts of FIG. 1 employed in the spinal implant system 10. Although the preferred embodiment illustrated in the figures is shown with only one plate 12 and bone fastener 18 and related elements, different numbers of any of these elements may be utilized without departing from the scope of the present invention. For example, a plurality of plates 12 can be used in conjunction with each other, or a greater or lesser number of bone fasteners 18 may be used depending upon the configuration of the plate 12 and medical problem to be addressed and/or any other factors. The present invention contemplates having at least one bone plate and two bone fasteners as well as two sliding elements 14, two stopping elements 20, and two locking elements 22, one of the elements 14, 20, 22 associated with each fastener 18.

Figure 3:
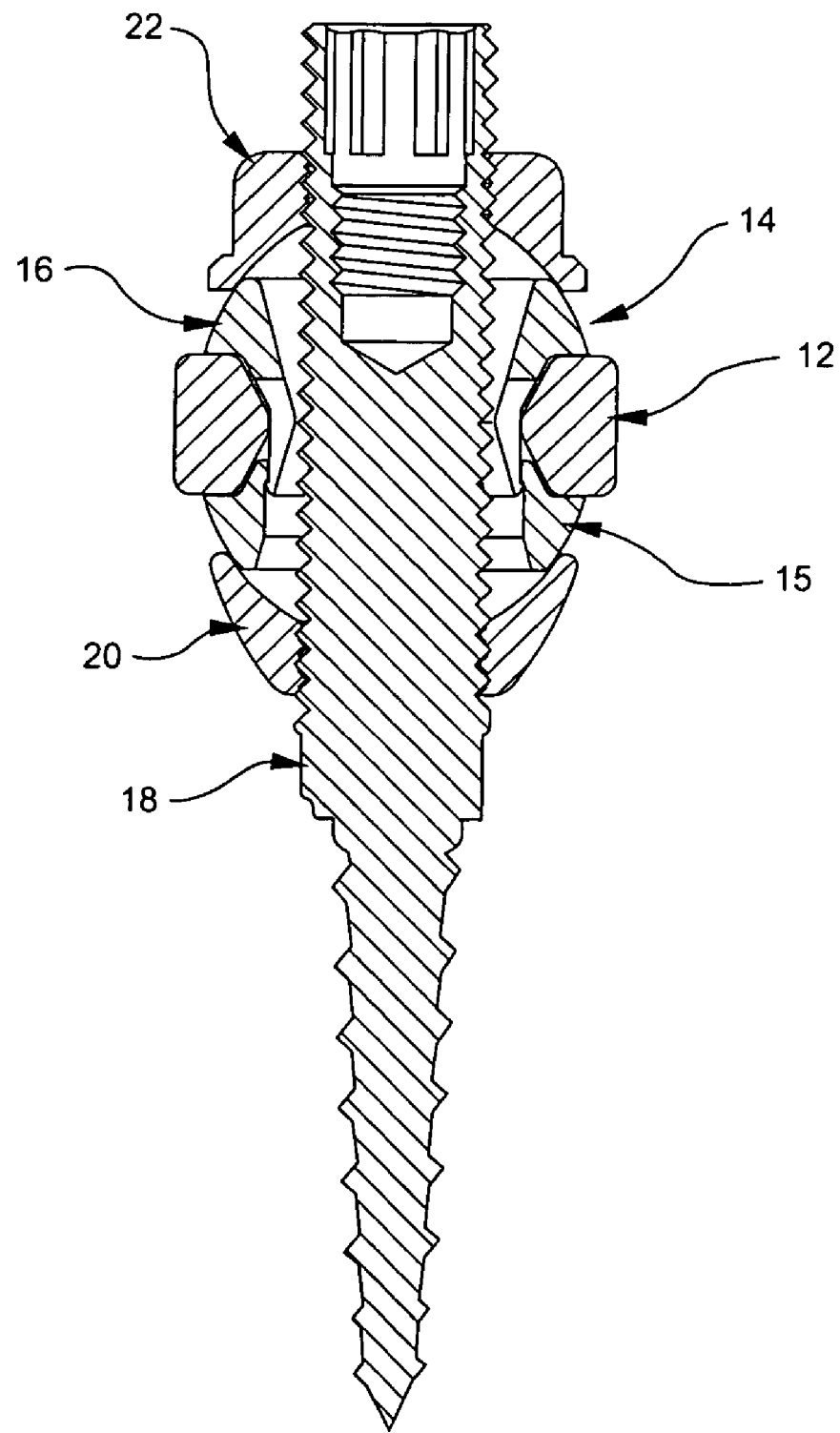
FIG. 3 is a cross-sectional view of the embodiment illustrated in FIG. 2 assembled.
Figure 4A:
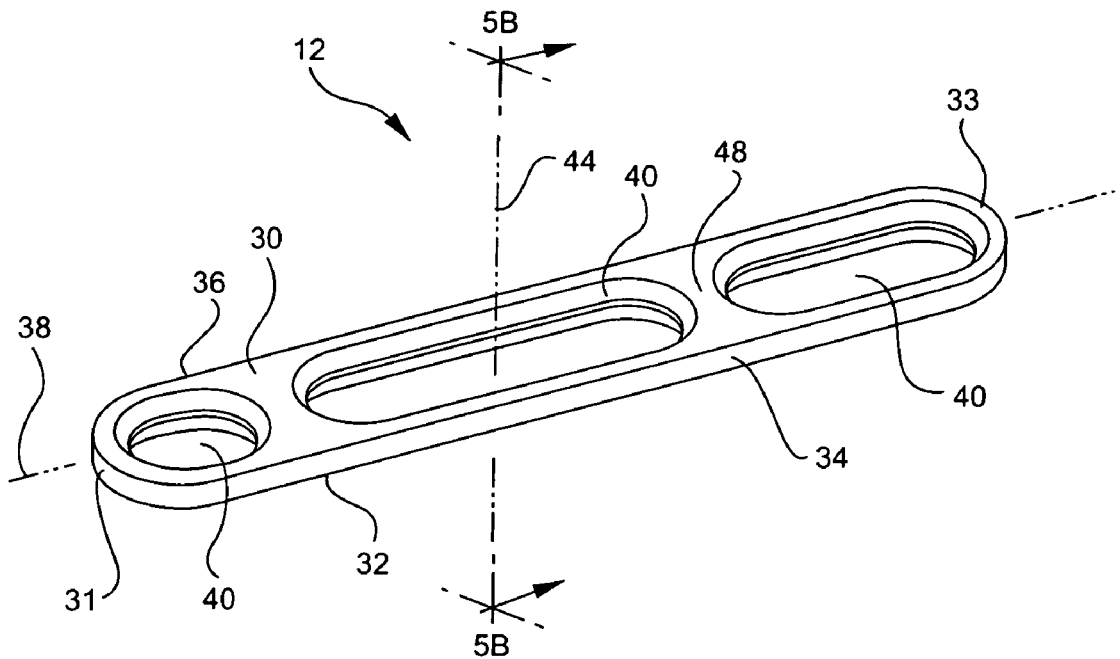
FIG. 4a is a perspective view of an elongated plate used in one embodiment of the present invention.
Figure 4B:
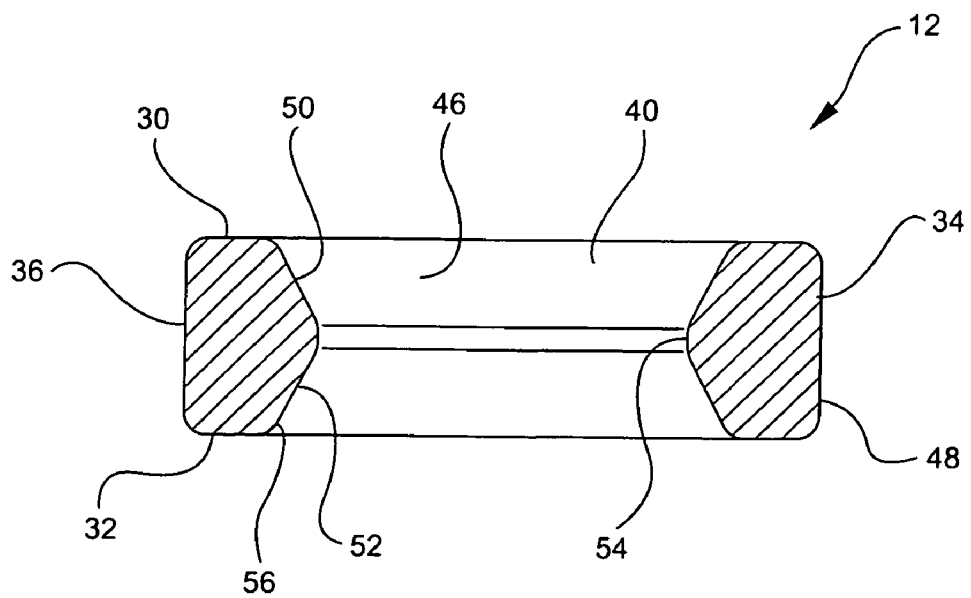
FIG. 4b is a cross-sectional view of the plate illustrated in FIG. 4a along lines 4-4.

FIG. 3 illustrates the cooperation and positioning of each element 14, 15, 20, 22 relative to the other on fastener 18 with plate 12 positioned along a longitudinal axis. Preferably this longitudinal axis is adjacent the longitudinal axis of a spinal column. Sliding element 14 is then positioned within apertures of the plate as will be discussed below. At this point, the top and bottom portions 15, 16 of sliding element 14 is capable of sliding back and forth about the plates' apertures 40. The stopping element 20 is positioned beneath the base portion 15 of the sliding element 14. The stopping element 20 is designed to be able to rotate about a curved exterior wall of the base portion 15 while still maintaining contact with base portion 15. Subsequently, a bone fastener 18 such as a bone screw is placed through an aperture of the sliding element 14 and engages the stopping element 20. Lastly, the locking element 22 is received by the bone fastener and translated downward until coming in contact with the top surface of portion 16 of the sliding element 14. Further discussion regarding specific features of each element as well as the cooperation between the elements will be discussed in further detail below.

Referring now to FIGS. 2, 3, 4a, and 4b, there is shown a preferred embodiment of plate 12. Plate 12 preferably has a generally rounded—rectangular or oval shape, an upper surface 30, a lower surface 32, a proximal end 31, and a distal end 33. Additionally, plate 12 has two opposing sides, right rail 34 and left rail 36. Plate 12 further includes at least one aperture or slot 40 extending along a longitudinal axis 38 of plate 12 from upper surface 30 to lower surface 32 and from end 31 to end 33. In a preferred embodiment, a plurality of bridges 48 may extend substantially perpendicular to right rail 34 and left rail 36, thereby creating a plurality of apertures 40 extending along axis 38. Apertures 40 have a generally open geometry enabling sliding element 14 to be placed within the aperture and slide axially along longitudinal axis 38. A circumferentially extending interior wall 46 of plate 12 may be substantially planar giving apertures 40 a uniform geometry, however, in a preferred embodiment, apertures 40 generally have a non-uniform about a central axis 44, which extends perpendicularly to the plane of plate 12 and axis 38. Again, although the interior wall 46 of plate 12 may be substantially parallel with exterior wall 48 of plate 12, in a preferred embodiment, interior wall 46 is inwardly tapered from both the top surface 30 and bottom surface 32. When describing the preferred embodiment of interior wall 46, reference is drawn to the interior of left rail 36, although it should be realized by those skilled in the art that right rail 34 and the ends of aperture 40 may have a substantially similar interior wall adjacent upper surface 30. Interior wall 46 includes an inwardly tapered first wall portion 50 which, in the preferred embodiment, ends adjacent the midway point between surfaces 30, 32. Likewise interior wall 46 further includes an inwardly tapered second wall 52 extending to said midway point from lower surface 32. Extending therebetween and connecting first wall 50 and second wall 52 is linking wall 54 which may be substantially planar and parallel to exterior wall 48.

In a preferred embodiment, first wall 50 and second wall 52, extend circumferentially about apertures 40 and have a concavity facing away from linking wall 54. Additionally, in the preferred embodiment, first wall 50 and second wall 52 include chamfered edges 56 connecting the walls to upper surface 30 and lower surface 32, respectively. This configuration of interior wall 46 allows for greater polyaxial motion of fastener 18 within plate 12 as will be described later.

Plate 12 is of sufficient length to bridge more than one vertebrae, as shown in FIG. 1, for which stabilization is required, and it would be appreciated, various dimensions of the plate and its features exist, all within the scope of the present invention. The plate 12 may be substantially planar as shown in FIG. 2 or have a concave shape as shown in FIG. 1.

The plate 12, as well as the other elements of the assembly, is preferably made from a biological inert material, for example, any metal customarily used for surgical devices and particularly those used for bone screws and pins, such as titanium or stainless steel. Other suitable materials include, but are not limited to, metal alloys, composite materials, ceramics, or carbon fiber materials.

With reference to FIGS. 5a and 5b, there is shown a preferred embodiment of a bone fastener 18. Bone fastener 18 is in the shape of a pedicle screw; however, various other fasteners may be utilized including a bone hook replacing the threaded bone engaging end of the bone screw. Preferably, bone fastener 18 has a threaded end 60 capable of anchoring the fastener into a vertebrae or similar bone structure and a opposing stem end 62. In a preferred embodiment stem end 62 includes an exterior thread 64 exposed along its surface. Bone fastener 18 may further include recess 66 for cooperating with a screwdriver, wrench, Allen key, or similar tool. Recess 66 may be in the form of a hexagon 67 as shown in the figures or alternatively, may be a slot or other shape including projections that allow the tools previously mentioned to mate to the bone fastener 18 and screw the bone fastener into a vertebral body 2. Bone fastener 18 may also have a top surface 68, which is substantially flat or in the alternative has a spherical configuration either concaved or convexed relative to threaded end 60.

Figure 6A:
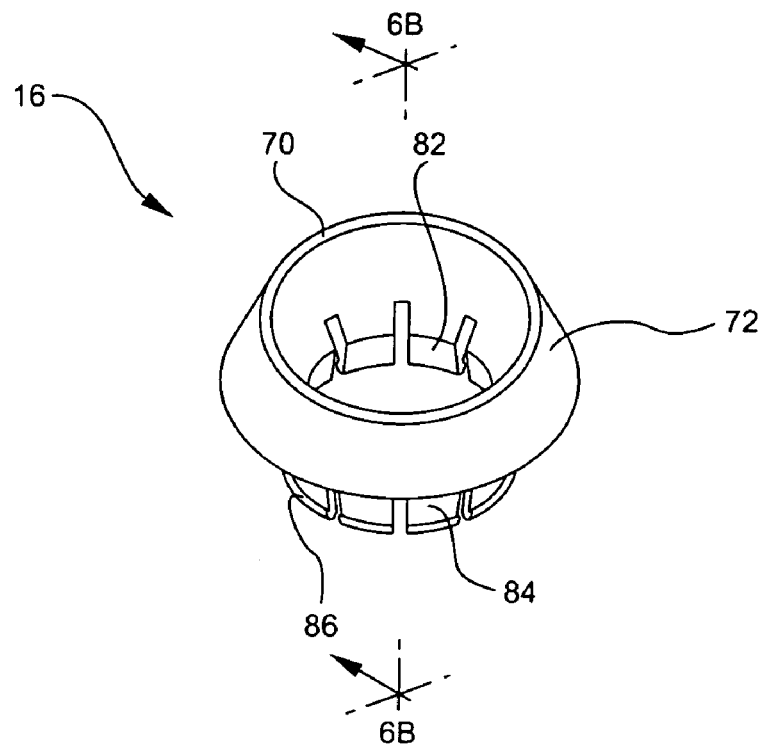
FIG. 6a is a perspective view of top portion of a sliding element used in one embodiment of the present invention.
Figure 6B:
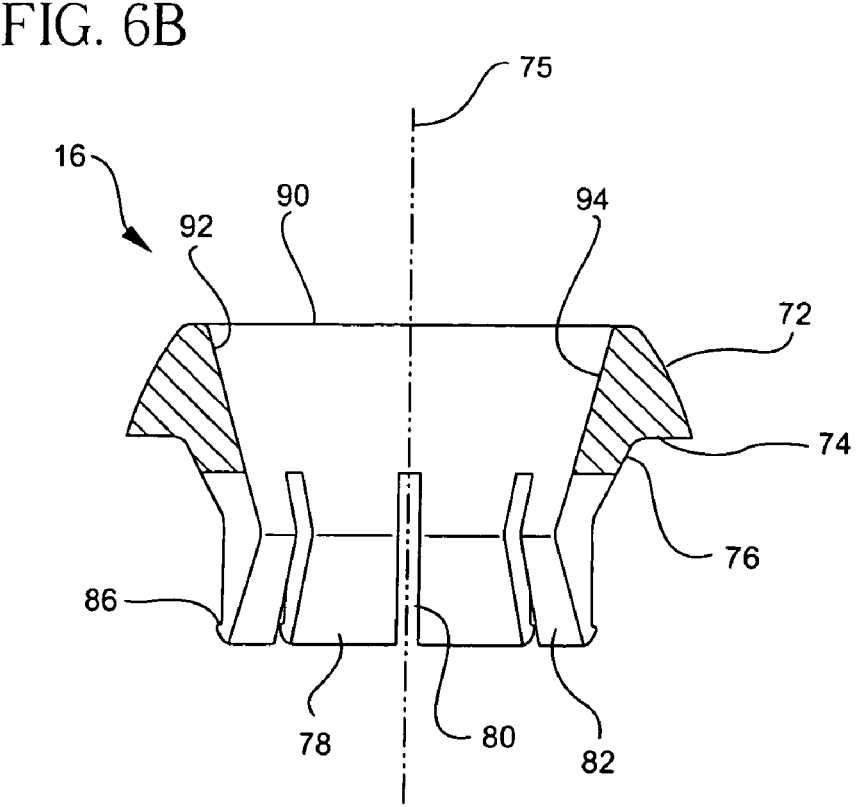
FIG. 6b is a cross-sectional view of the embodiment shown in FIG. 6a along lines 6-6.

Referring now generally to FIGS. 2, 3, 6a, and 6b, there is shown a preferred embodiment of top portion 16 of sliding element 14. Top portion 16 preferably includes a rim 70 extending around the circumference of top portion 16. Adjacent rim 70 is skirt 72, which extends axially and radially outwardly around top portion 16 and in the preferred embodiment has a part-spherical outer surface relative to a central longitudinal axis 75 of top portion 16. At the lower end of skirt 72 is an inwardly extending shoulder 74. Shoulder 74 extends radially inward to a substantially flat wall 76 for cooperating with interior wall 50 of plate 12. In the preferred embodiment, portion 50 of wall 46 is tapered thus shoulder 74 is adjacent to an inwardly tapered wall 76, as shown in FIG. 6B.

The top portion 16 of sliding element 14 may further include a plurality of fingers 78 extending around the circumference downwardly from tapered wall 76. Fingers 78 are separated by slots 80 located adjacent and between each finger 78. Each finger 78 includes an outwardly tapered wall 82 and an exterior wall 84. In a preferred embodiment, exterior wall 84 of fingers 78 includes a lip 86 extending outwardly from a bottom portion of fingers 78. It is possible for lip 86 to be disposed along only a middle portion of fingers 78 or be located on few than all the fingers.

Preferred top portion 16 further includes a circular aperture 90 extending from rim 70 through the lower portion of fingers 78. Aperture 90 has an inwardly tapered axially extending interior wall 92 which at least partially defining the axial extent of aperture 90 and intersects with outwardly tapered walls 82 of fingers 78.

Figure 7A:
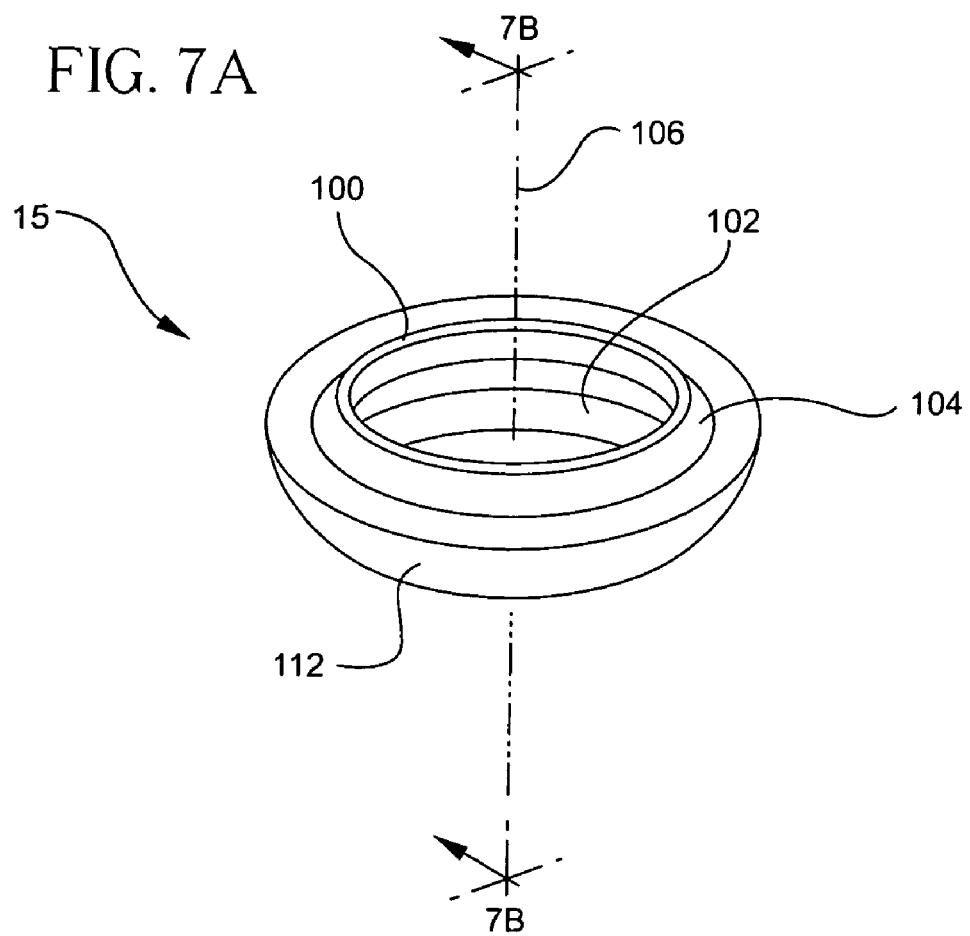
FIG. 7a is a perspective view of the bottom portion of the sliding element used in one embodiment of the present invention.
Figure 7B:
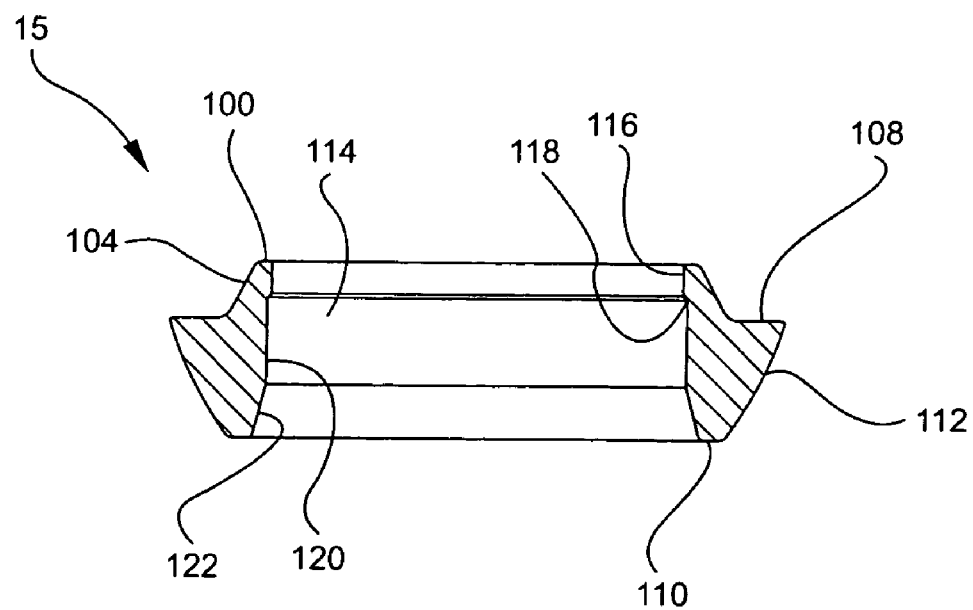

As illustrated in FIGS. 7a and 7b, base portion 15 of sliding element 14 has a rim 100 extending around the top of an aperture 102, which aperture extends through base portion along a longitudinal axis 106. A tapered skirt 104 extends radially outwardly from rim 100 and preferably has an outer surface for engaging surface 52 of plate 12. Adjacent to skirt 104 is shoulder 108, which extends outward from skirt 104 and away from longitudinal axis 106. Extending between shoulder 108 and a bottom surface 110 of element 15 is exterior wall 112. Bottom surface 110 extends radially around the lower surface of base portion 15. In a preferred embodiment the exterior surface of wall 112 extends around base portion 15 and has a part-spherical configuration relative to longitudinal axis 106.

Aperture 102 extends through element 15 from rim 100 to bottom surface 110 and is at least partially defined by cylindrical interior wall 114. In the preferred embodiment, interior wall 114 is adjacent an abutting cylindrical wall 116 of a small diameter. The differences between the diameters create a lip 118. Lip 118 may extend completely around the circumference of abutting wall 116 or only partially. Lastly, in the preferred embodiment outwardly surface 122 extends downwardly from wall 114 to the surface 110.

The sliding element 14 is preferably designed so that top portion 16 is placed within an aperture 40 of plate 12 with shoulder 74 resting either against or near upper surface 30 of plate 12. Base portion 15 is subsequently snap-fitted to top portion 16. Specifically, aperture 102 of base portion 15 slidably receives fingers 78 with wall 116 compressing fingers 78 within aperture 102. Top portion 14 is then translated downward onto aperture 102 of base 15 or base portion 15 is translated upwardly over fingers 78 until lip 86 engages shoulder 118 of base 15.

Without the compressive inward force generated by wall 116 compressing fingers 78, the fingers expand outwardly either back to their at-rest position or preferably closer to their at-rest position but still exhibiting a compressive force to keep the parts together. Lip 86 also deflects outward under the shoulder 118, and subsequently locks top portion 14 to base portion 15 at least so the top portion 14 cannot be moved upward without a lateral inward force being applied to fingers 78. Although in a preferred embodiment, the sliding element 14 has been described as including two portions snap-fitted together, it would not go beyond the scope of the present invention if the two bodies were assembled using alternate techniques such as being screwed together, locked together in another manner, or even consisting of a one-piece assembly pre-molded within aperture 40 of the plate 12.

In either situation, sliding element 14 is capable of sliding in the direction of longitudinal axis 38 within aperture 40 with shoulder 74 and shoulder 108 sliding along upper surface 30 and lower surface 32 respectively.

Figure 8A:
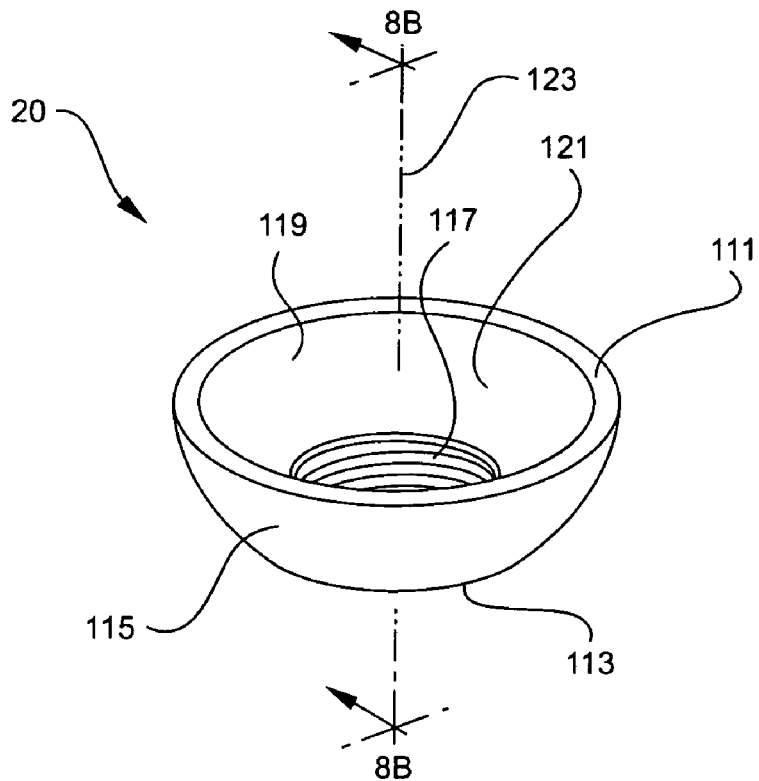
FIG. 8a is a perspective view of a stopping element.
Figure 8B:
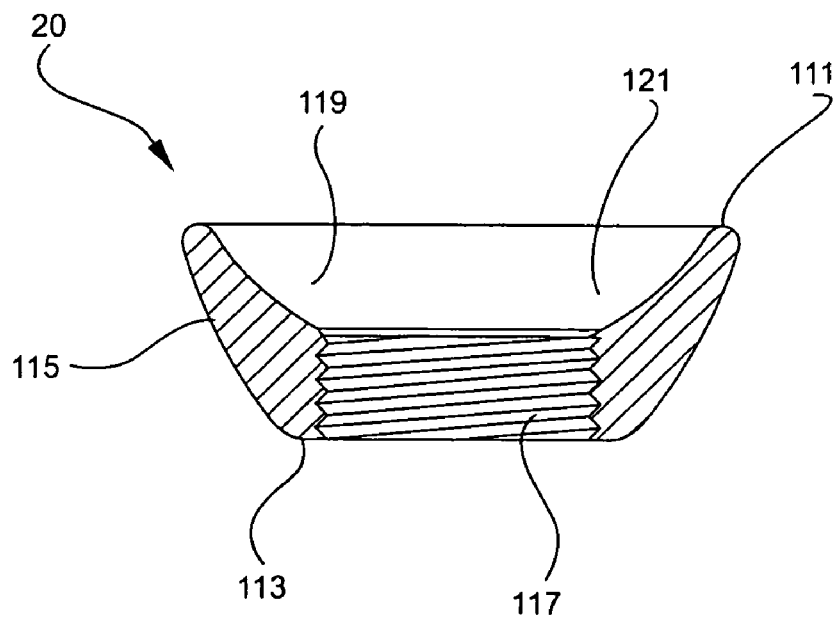

With reference to FIGS. 8a and 8b, there is shown an embodiment of a stopping element 20. Stopping element 20 includes a top surface 111 and a bottom surface 113. Extending therebetween and adjacent to top surface 111 and bottom surface 113 is exterior wall 115. In a preferred embodiment exterior wall 115 extends circumferentially around stopping element 20 and preferably is part-spherical relative to longitudinal axis 117 extending through the center of the stopping element but could be of any shape. A concave surface 119 extends downwardly and inwardly from surface 111 towards bottom surface 113. As with exterior wall 115 in a preferred embodiment interior wall 119 radially extends and is part-spherical relative to longitudinal axis 123. Interior wall 119 ends within stopping element 20 intermediate surfaces 111 and 113. Aperture 121 extends through the remainder of stopping element 20 as a threaded bore with a plurality of threads 117 extending between interior wall 119 and bottom surface 113. In a preferred embodiment, the radius of curvature of interior wall 119 is substantially equal to the radius of curvature of exterior wall 112 of base portion 15. This configuration permits element 20 to rotate on base portion 15 such that longitudinal axis 117 of stopping element 20 is angularly offset from longitudinal axis 106 of base portion 15.

Figure 9A:
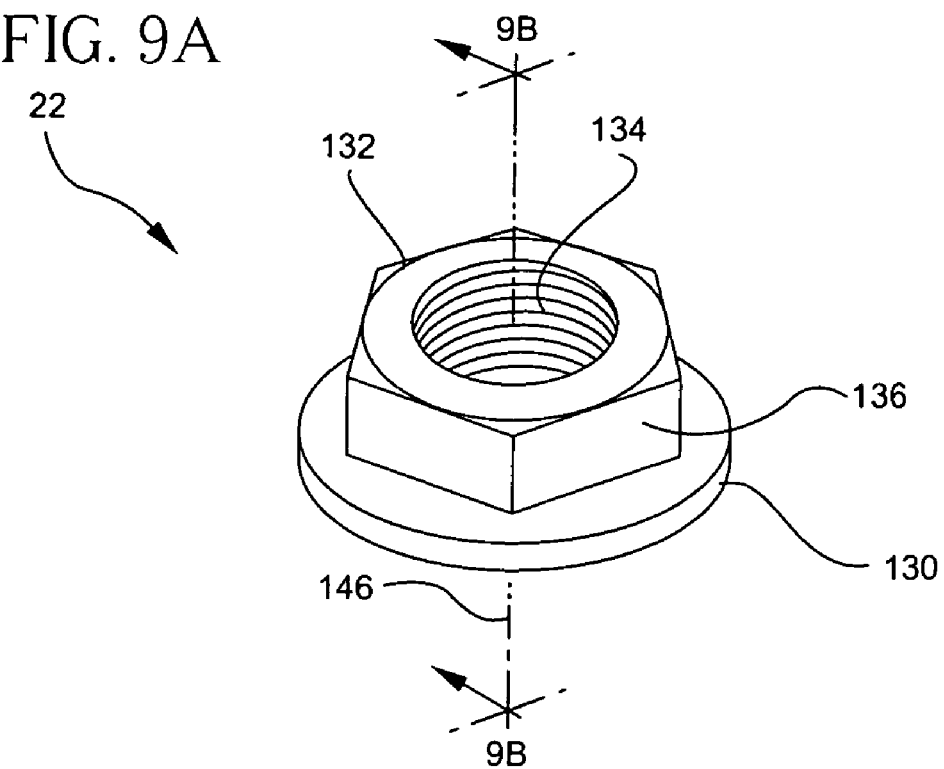
FIG. 9a is a perspective view of a locking element used in one embodiment of the present invention.
Figure 9B:
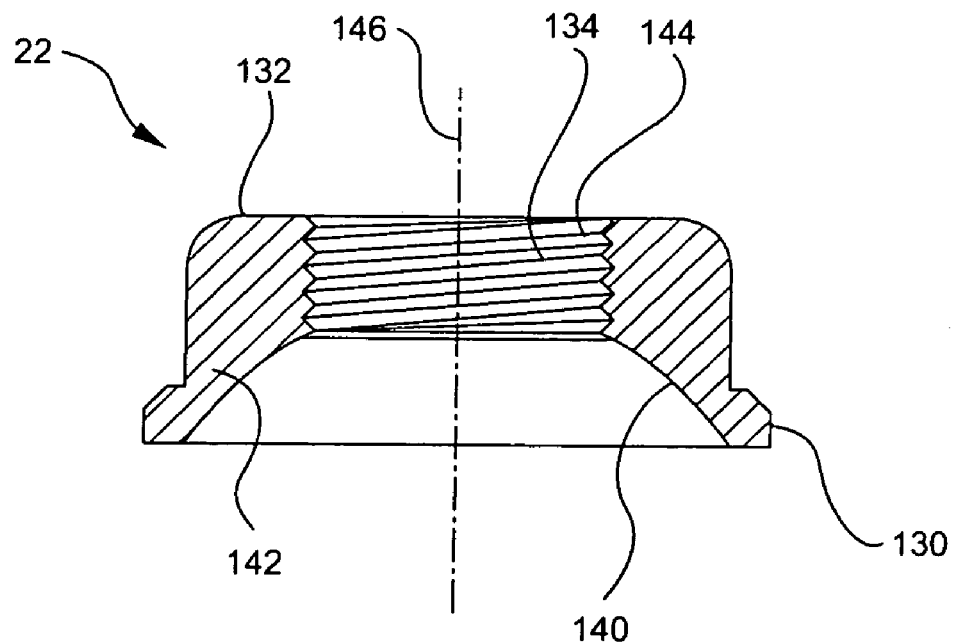

As seen in FIGS. 9a and 9b, preferred locking element 22 includes base 130 and cap 132. The locking element 22 also includes an aperture 134 extending longitudinally through the locking element and about longitudinal axis 146. Additionally, cap 132 may include a drive surface 136, such as a hexagon, adjacent to base 130. Aperture 134 includes a radially inwardly extending part-spherical wall 140 defining the bottom portion of aperture 134. Wall 140 extends from base 130 to a threaded bore 144. Aperture 134 further includes a threaded portion 144 defining the upper portion of aperture 134. The threads of portion 144 and threads 117 match threads 64 of fastener 18.

In a preferred embodiment, the curvature of interior wall 140 is substantially equal to the curvature of skirt 72 of top portion 16. This configuration permits element 22 to rotate on top portion 16 so that the longitudinal axis of the locking element 22 is angularly off-set from the longitudinal axis of top portion 16 while still maintaining a high degree of cooperation between the two elements.

In a method of use of the present assembly, a bone fastener 18 is engaged to vertebral body 2 preferably after a hole is pre-drilled into the vertebral body. Bone fastener 18 is translated downward into vertebral body 2 until a desired depth has been reached. Stopping nut 20 is then threadably engaged to stem end 62 of bone fastener 18. The stopping nut 20 is translated downward along the stem end 62 until its desired location is reached. Either prior to these steps of operation or during the same, sliding element 14 is assembled within aperture 40 of plate 12 and is still able to slide back and forth in the apertures along longitudinal axis 38 of plate 12. Positioned within plate 12, sliding element 14 is lowered about stem end 62 of bone fastener 18 with apertures 90 and 102 of top portion 16 and base portion 15, respectively slidably receiving stem end 62. Apertures 90 and 102 are preferably provided with a minimum diameter greater than the maximum diameter of stem end 62, to permit bone fastener 18 to be angularly off-set from sliding element 14 (i.e., their longitudinal axes are at an angle). Sliding element 14 and plate 12 are lowered until base portion 15 contacts or abuts stopping nut 20. Specifically, exterior wall 112 of base portion 15 is placed adjacent and in contact with interior wall 119 of stopping nut 20.

As can be viewed by the orientation of the two curved walls, i.e., exterior surface 112 and interior surface 119, the orientation of the stopping nut 20 relative base portion 15 may be at various angles. Specifically, stopping nut 20 can rotate with respect to exterior surface 112 of the base portion 15 and still maintain contact at at least two discrete locations. The orientation of the stopping nut 20 relative to the base portion 15 depends on the relative angle between plate 12 and fastener 18 wherein the bone fastener may be angled into the vertebral body at an angle different than 90° (perpendicular) relative to the positioning of plate 12. More specifically, since sliding element 14 has apertures 90 and 102, each aperture having a greater minimum radius than the radius of stem end 62 of bone fastener 18, bone fastener 18 may be positioned at varying angles relative to sliding element 14. However, due to the fact that the stopping nut 20 is threadably mated to stem end 62, stopping nut 20 and bone fastener 18 maintain a co-axial relationship having a common longitudinal axis once assembled together.

In order to lock the assembly together, locking nut 22, specifically aperture 134 is lowered downward to receive stem end 62. Threads 64 of stem end 62 mate with threads 144 of locking element 22. Locking element 22 is translated downward along a longitudinal axis 63 passing through the center of bone fastener 18 until coming in contact with surface 72 of sliding element 14. Specifically, element 22 is threaded onto shaft 62 until interior wall 140 comes in contact with skirt 72 of top portion 16. Similar to the above-described cooperating relationship between stopping element 20 and base portion 15, the locking element 22 may be oriented along various angular positions relative to skirt 72 so that while locking element 22 shares a common central axis with bone fastener 18, the central longitudinal axes of locking element 22 and top portion 16 of element 14 may be offset from one another.

In order to lock the elements of the assembly relative to one another, locking element 22 is translated further downward applying an increased force against top portion 16. This force is translated downward through plate 12, base portion 15 until finally reaching stopping nut 20. At this point, stopping nut 20 applies a reactive force upward against the elements causing top portion 16 and base portion 15 to clamp onto plate 12. Specifically, shoulder 74 of top portion 16 contacts upper surface 30 of plate 12 while bottom shoulder 108 contacts lower surface 32 of plate 12. Continued translation of locking element 22 downward along stem end 62 locks all the elements relative to one another.

Prior to tightening the locking element 22 completely, the assembly 10 may be loosely pre-assembled as a unit or partially pre-assembled. Threaded end 60 of bone fastener 18 may then preferably be engaged into a pre-drilled hole located within the vertebral body 2. The bone fastener 18 may be translated downward into the vertebral body by using a tool received in recess 66 of bone fastener 18. Upon reaching a desired position for the bone fastener 18, the rest of the assembly may be oriented in a desired relationship with once again the possibility of a longitudinal axis for the bone fastener 18, locking nut 20 and locking nut 22 being offset from a central longitudinal axis shared by plate 12 and sliding component 14.

In either method of use, because of the exposure of top surface 68 of bone fastener 18, the bone fastener may be re-positioned relative to its depth in a vertebral body after the unit has been assembled but prior to being completed locked.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic bone plate system, comprising:
a bone plate for placement adjacent one or more vertebral bodies, having a first aperture extending along a longitudinal axis and an upper and lower surface;
a sliding element having a top portion and a base portion, and an aperture extending along a central axis therethrough, said sliding element adapted for being placed adjacent said bone plate aperture and said base portion having a convex surface;
a bone fastener having a longitudinal axis and adapted for connecting said bone plate to a vertebral body, said bone fastener having a stem and a bone engaging portion, wherein a diameter of said stem is less than a cross-section of said sliding element aperture so that said stem may be oriented within said sliding element aperture at a plurality of angles;
a stopping element having a concave surface engageable with said convex surface of said sliding element base portion such that the stopping element can rotate about said convex surface of the base portion thereby allowing the bone fastener to be positioned and locked in the sliding element aperture at a plurality of different angles, the stopping element also having a bore adapted for receiving said stem portion of said bone fastener, said bore enabling said stopping element to translate along the longitudinal axis of said bone fastener such that said stopping element may be located at different positions along said bone fastener; and
a locking element engageable with said top portion having a bore adapted for receiving said stem portion of said bone fastener.

2. The orthopedic bone plate system according to claim 1, wherein said sliding element includes a compression member and locking member, said compression member including said top portion, said locking member including said base portion, wherein said compression member is adapted to engage said locking member.

3. The orthopedic bone plate system according to claim 1, wherein a plurality of fingers extend in a direction parallel to said central axis of said compression member from said top portion toward said base portion.

4. The orthopedic bone plate system according to claim 3, wherein said fingers are tapered inwardly toward said central axis.

5. The orthopedic bone plate system according to claim 1, wherein said top and base portions include an inwardly tapered wall.

6. The orthopedic bone plate system according to claim 1, wherein said top portion includes a radially outwardly extending curved wall.

7. The orthopedic bone plate system according to claim 1, wherein said base portion includes a radially outwardly extending curved wall.

8. The orthopedic bone plate system according to claim 3, wherein said fingers have a ridge extending at least partially around an outer circumference thereof, said ridge adapted to engage a lip extending at least partially around an inner circumference of said base portion.

9. The orthopedic bone plate system according to claim 1, wherein said sliding element aperture has a minimum diameter greater than the maximum diameter of said stem of said bone fastener.

10. The orthopedic bone plate system according to claim 1, wherein said locking element includes a base and a cap.

11. The orthopedic bone plate system according to claim 1, wherein said locking element has a concave wall at least partly surrounding said bore.

12. The orthopedic bone plate system according to claim 11, wherein said locking element includes threads mateable to threads disposed on said stem of said bone fastener.

13. The orthopedic bone plate system according to claim 12, wherein said locking element threadably engages said stem of said bone fastener, wherein said concave surface of said locking element is adapted for cooperating with said sliding element spherical top portion at a plurality of different angles.

14. The orthopedic bone plate system according to claim 1, wherein said stopping element has an inner spherical wall at least partially surrounding said stopping element bore, wherein said stopping element inner spherical wall is adapted for cooperating with a spherical surface of said sliding element base portion at a plurality of different angles.

15. The orthopedic bone plate system according to claim 1, wherein said stopping element has threads mateable to threads on said stem of said bone fastener.

16. The orthopedic bone plate system according to claim 1, wherein said stopping element, said locking element and said bone fastener are adapted for being locked on said sliding element relative to one another, wherein said stopping element, said locking element and said bone fastener may be positioned about said sliding element aperture at a plurality of angles.

17. The orthopedic bone plate system according to claim 1, wherein said bone plate has an interior wall adapted for cooperating with said top and base portion of said sliding element.

18. The orthopedic bone plate system according to claim 1, wherein said top portion and said base portion each include a radially extending shoulder adapted for cooperating with said upper and lower surface of said bone plate.

19. The orthopedic bone plate system according to claim 1, wherein said sliding element is adapted for sliding along said bone plate aperture along the longitudinal axis.

20. The orthopedic bone plate system according to claim 1, including a first set of threads disposed on said stem portion and a second and third set of threads disposed on said stopping element bore and said locking element bore respectively, wherein said first set of threads engage said second and third set of threads when said stem portion is placed within said locking element bore and said stopping element bore.

21. The orthopedic bone plate system according to claim 1, wherein said bone fastener includes a top surface having a recess adapted for engaging an instrument or tool.

22. The orthopedic bone plate system according to claim 21 wherein said recess is capable of being accessed after the bone plate system is assembled.

23. The orthopedic bone plate system according to claim 1, wherein said bone plate has at least two apertures separated by a bridge extending transverse to the longitudinal axis.

24. The orthopedic bone plate system according to claim 1, wherein said bone plate is curved in an anterior and posterior direction.

25. A system for coupling a bone fastener to a bone plate comprising:
   a bone plate having a bone facing surface and an elongate opening therethrough extending along a longitudinal axis generally parallel to said bone facing surface;
   an insert slidable in said elongate opening, said insert having a first part with a part-spherical outer surface a base portion having a second spherical surface and an internal bore extending along an axis transverse to said elongate opening in said plate, said second spherical surface facing the bone;
   a bone fastener having a first bone engaging portion and a second portion for extending through said bore in said insert;
   a positioning means for positioning a height of said bone plate relative to a vertebral body, said positioning means allowing said height of said bone plate relative to said vertebral body to be adjusted without movement of said bone fastener said positioning means having a third spherical surface facing away from the bone, said third spherical surface being adapted to rotatably engage the second spherical surface thereby allowing the bone fastener to be positioned and locked in the insert at a plurality of different angles; and
   a locking element mounted on said second portion of said fastener, said locking element having a part-spherical surface for engaging said spherical outer surface of said insert, said locking element moveable towards said bone plate along said second portion of said fastener for engaging and moving said insert first part into engagement with said bone plate.

26. The system as set forth in claim 25, wherein said insert further comprises a second part mounted on said fastener and engageable with said bone facing plate surface, said first and second insert parts moveable towards one another for clamping said bone plate therebetween.

27. The system as set forth in claim 26, wherein said second portion of said bone fastener is threaded and said locking element includes threaded bore for threadably engaging said threads of said fastener second portion.

28. The system as set forth in claim 27, wherein said first and second insert parts each have outer tapered surfaces for engaging tapered surface in said aperture.

29. A method for implanting an orthopedic implant system in a bone comprising:
   a. engaging a bone engaging portion of a bone fastener having a first bone engaging portion and a second portion extending from said bone engaging portion along a longitudinal axis to a bone;
   b. providing a bone plate having a bone facing surface and an elongated opening therethrough extending along a longitudinal axis generally parallel to said bone facing surface;
   c. placing an insert slidable in said elongate opening on said bone fastener, said insert having a first part with a spherical outer surface, a base portion having a second spherical surface and an internal bore extending along an axis transverse to said elongate opening in said plate, said second spherical surface being convex and facing the bone;

d. positioning said insert down said bone fastener second portion, said insert bore being adapted for receiving said second portion;
e. engaging a positioner onto said bone fastener, said positioner having an engagement element that allows said positioner to engage said bone fastener and translate along the longitudinal axis of the bone fastener said positioner having a concave spherical surface, said concave spherical surface being adapted to rotatably engage the second spherical surface thereby allowing the bone fastener to be positioned and locked in the insert at a plurality of different angles;
f. orienting said bone plate and said insert into a desired position with respect to said bone fastener, wherein the step of orienting the bone plate may include moving the positioner relative to the bone fastener; and
g. mounting a locking element on said second portion of said fastener, said locking element have a spherical surface for engaging said spherical outer surface of said insert, said locking element moveable towards said bone plate along said second portion of said fastener for engaging and moving said insert first part into engagement with said bone plate.

30. The method according to claim 29, comprising the step of adjusting said bone fastener relative to said bone after said insert receives said second portion.

31. The method according to claim 29, wherein said insert includes a second part having a bore for receiving said bone fastener second portion, said second part engageable with said bone facing plate surface, said first and second insert parts moveable towards one another for clamping said bone plate the therebetween.

* * * * *

UNITED STATES PATENT AND TRADEMARK OFFICE
CERTIFICATE OF CORRECTION

PATENT NO.       : 7,491,221 B2                                      Page 1 of 2
APPLICATION NO.  : 10/806736
DATED            : February 17, 2009
INVENTOR(S)      : Jérôme David It is certified that error appears in the above-identified patent and that said Letters Patent is hereby corrected as shown below:

At Column 2, Line 11, replace "include" with --including--.
At Column 2, Line 17, replace "having" with --has--.
At Column 2, Line 40, replace "having" with --has--.
At Column 2, Line 49, replace "curve" with --curved--.
At Column 2, Line 50, replace "curve" with --curved--.
At Column 2, Line 64, after "elements" please insert --'--.
At Column 3, Line 39, replace "including" with --includes--.
At Column 3, Line 46, replace "having" with --has--.
At Column 3, Line 62, replace "surface" with --surfaces--.
At Column 4, Line 7, replace "having" with --has--.
At Column 4, Line 15, replace "having" with --has--.
At Column 4, Line 22, replace "receive" with --receives--.
At Column 4, Line 25, replace "being" with --is--.
At Column 5, Line 42, replace "is" with --are--.
At Column 6, Line 3, replace "slide" with --slid--.
At Column 6, Line 7, replace "have a" with --are--.
At Column 6, Line 27, after "52", delete ",".
At Column 6, Line 36, after "appreciated" delete ",".
At Column 6, Line 36, after "appreciated" insert --that--.
At Column 6, Line 53, replace "a" with --an--.
At Column 6, Line 59, after "or" insert --,--.
At Column 7, Line 21, replace "few" with --fewer--.
At Column 7, Line 25, replace "defining" with --defines--.
At Column 7, Line 30, after "portion" insert --15--.
At Column 9, Line 32, after "134" insert --,--.
At Column 12, Line 13, after "surface" insert --,--.
At Column 12, Line 25, after "fastener" insert --,--.
At Column 12, Line 34, after "element" insert --being--.
At Column 12, Line 41, after "parts" insert --being--.
At Column 12, Line 46, after "includes" insert --a--.
At Column 12, Line 49, replace "surface" with --surfaces--.

Signed and Sealed this

Twenty-seventh Day of April, 2010

David J. Kappos
*Director of the United States Patent and Trademark Office*

At Column 14, Line 4, after "element" insert --being--.
At Column 14, Line 13, after "part" insert --being--.
At Column 14, Line 15, after "part" insert --being--.